US010420914B1

(12) United States Patent
Koutsouradis et al.

(10) Patent No.: US 10,420,914 B1
(45) Date of Patent: Sep. 24, 2019

(54) CALYPSO BOWL SYSTEM

(71) Applicants: Alkiviadis Koutsouradis, Palm Harbor, IN (US); Theodore Panagiotopoulos, Clearwater, FL (US); Adarsh Verma, Clearwater, FL (US); Jerry Chung, Clearwater, FL (US)

(72) Inventors: Alkiviadis Koutsouradis, Palm Harbor, IN (US); Theodore Panagiotopoulos, Clearwater, FL (US); Adarsh Verma, Clearwater, FL (US); Jerry Chung, Clearwater, FL (US)

( * ) Notice: Subject to any disclaimer, the term of this patent is extended or adjusted under 35 U.S.C. 154(b) by 0 days.

(21) Appl. No.: 15/418,262

(22) Filed: Jan. 27, 2017

Related U.S. Application Data

(60) Provisional application No. 62/292,994, filed on Feb. 9, 2016.

(51) Int. Cl.
*A61M 25/00* (2006.01)
*A61M 25/09* (2006.01)
*B65H 75/36* (2006.01)

(52) U.S. Cl.
CPC .......... *A61M 25/002* (2013.01); *A61M 25/09* (2013.01); *B65H 75/364* (2013.01); *A61M 2025/0019* (2013.01); *A61M 2205/583* (2013.01)

(58) Field of Classification Search
USPC ................................. 206/364, 571, 210, 365
See application file for complete search history.

(56) References Cited

U.S. PATENT DOCUMENTS

| | | | | |
|---|---|---|---|---|
| 4,226,328 A | * | 10/1980 | Beddow | A61F 17/00 206/364 |
| 5,125,416 A | * | 6/1992 | Phillips | A61B 50/30 206/364 |
| 5,738,213 A | * | 4/1998 | Whiting | A61M 25/002 206/210 |
| 6,068,121 A | * | 5/2000 | McGlinch | A61M 25/002 206/364 |
| 6,569,106 B1 | * | 5/2003 | Ullman | A61M 25/09 600/585 |
| 8,662,306 B2 | * | 3/2014 | Agrawal | B65D 85/00 206/370 |
| 2006/0278546 A1 | * | 12/2006 | State | A61M 25/002 206/364 |
| 2009/0071851 A1 | * | 3/2009 | Maki | A61M 25/002 206/210 |
| 2012/0312703 A1 | * | 12/2012 | Koellhofer | A61M 25/002 206/210 |
| 2014/0374295 A1 | * | 12/2014 | Lessne | B65D 85/671 206/364 |

* cited by examiner

*Primary Examiner* — Jacob K Ackun

(57) ABSTRACT

An exterior bowl has a closed bottom, an open top, and a side wall there between. An exterior annular flange extends radially outwardly from the open top of the exterior bowl. An interior bowl has an open bottom, an open top, and a side wall there between. An interior annular flange extends radially outwardly from the open top of the interior bowl. The open bottom of the interior bowl is coupled to the closed bottom of the exterior bowl to create an annular chamber between the side wall of the exterior bowl and the side wall of the interior bowl. Tubing within the chamber in a spiral configuration removably receives a plurality of surgical wires. Each of the surgical wires has an upper extent extending upwardly and out of the chamber for being grasped and extracted from the tubing.

7 Claims, 3 Drawing Sheets

CALYPSO BOWL SYSTEM

RELATED APPLICATION

The present application claims the priority of Provisional Application No. 62/292,994 filed Feb. 9, 2016, the subject matter of which is incorporated herein by reference.

BACKGROUND OF THE INVENTION

Field of the Invention

The present invention relates to a Calypso Bowl System and more particularly pertains to supporting a plurality of surgical wires and dispensing individual surgical wires from the plurality of surgical wires. The supporting and dispensing is done in a safe, sanitary, convenient, and economical manner.

Description of the Prior Art

The use of bowl systems of known designs and configurations is known in the prior art. More specifically, bowl systems of known designs and configurations previously devised and utilized for the purpose of supporting and dispensing surgical guide wires are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, they do not describe a Calypso Bowl System that allows the supporting a plurality of surgical wires and dispensing individual surgical wires from the plurality of surgical wires in a safe, sanitary, convenient, and economical manner.

In this respect, the Calypso Bowl System according to the present invention substantially departs from the conventional concepts and designs of the prior art, and in doing so provides an apparatus primarily developed for the purpose supporting a plurality of surgical wires and dispensing individual surgical wires from the plurality of surgical wires in a safe, sanitary, convenient, and economical manner.

Therefore, it can be appreciated that there exists a continuing need for a new and improved Calypso Bowl System which can be used for supporting a plurality of surgical wires and dispensing individual surgical wires from the plurality of surgical wires in a safe, sanitary, convenient, and economical manner. In this regard, the present invention substantially fulfills this need.

SUMMARY OF THE INVENTION

In view of the foregoing disadvantages inherent in the known types of bowl systems of known designs and configurations now present in the prior art, the present invention provides an improved Calypso Bowl System. As such, the general purpose of the present invention, which will be described subsequently in greater detail, is to provide a new and improved Calypso Bowl System and method which has all the advantages of the prior art and none of the disadvantages.

To attain this, the present invention essentially comprises a Calypso Bowl System. From a broad perspective, first provided is an exterior bowl having a closed bottom, an open top, and a side wall there between. An exterior annular flange extends radially outwardly from the open top of the exterior bowl. Next provided is an interior bowl having an open bottom, an open top, and a side wall there between. An interior annular flange extends radially outwardly from the open top of the interior bowl. The open bottom of the interior bowl is coupled to the closed bottom of the exterior bowl to create an annular chamber between the side wall of the exterior bowl and the side wall of the interior bowl. Tubing is provided within the chamber in a spiral configuration removably receiving a plurality of surgical wires. Each of the surgical wires has an upper extent extending upwardly and out of the chamber for being grasped and extracted from the tubing.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved Calypso Bowl System which has all of the advantages of the prior art bowl systems of known designs and configurations and none of the disadvantages.

It is another object of the present invention to provide a new and improved Calypso Bowl System which may be easily and efficiently manufactured and marketed.

It is further object of the present invention to provide a new and improved Calypso Bowl System which is of durable and reliable constructions.

An even further object of the present invention is to provide a new and improved Calypso Bowl System which is susceptible of a low cost of manufacture with regard to both materials and labor, and which accordingly is then susceptible of low prices of sale to the consuming public, thereby making such Calypso Bowl System economically available to the buying public.

Lastly, even still another object of the present invention is to provide a Calypso Bowl System for supporting a plurality of surgical wires and dispensing individual surgical wires from the plurality of surgical wires in a safe, sanitary, convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
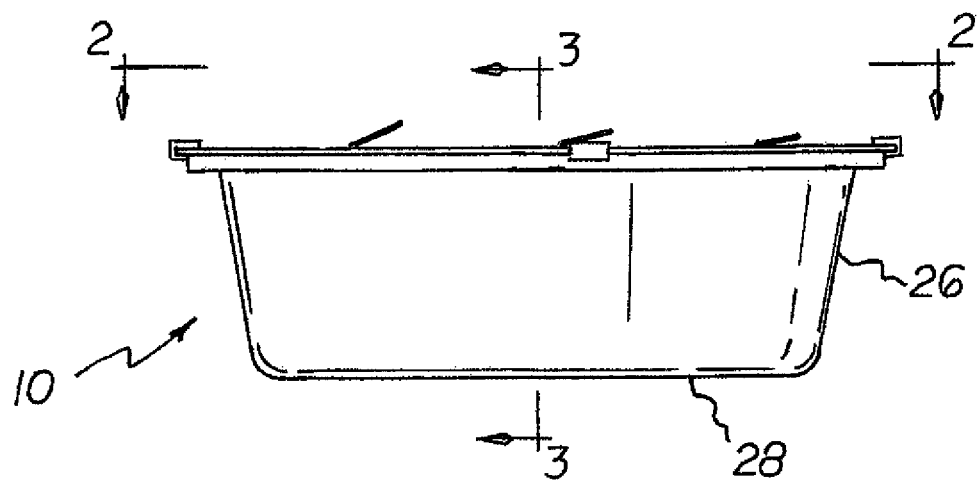
FIG. 1 is a side elevational view of a Calypso Bowl System constructed in accordance with the principles of the present invention.
Figure 2:
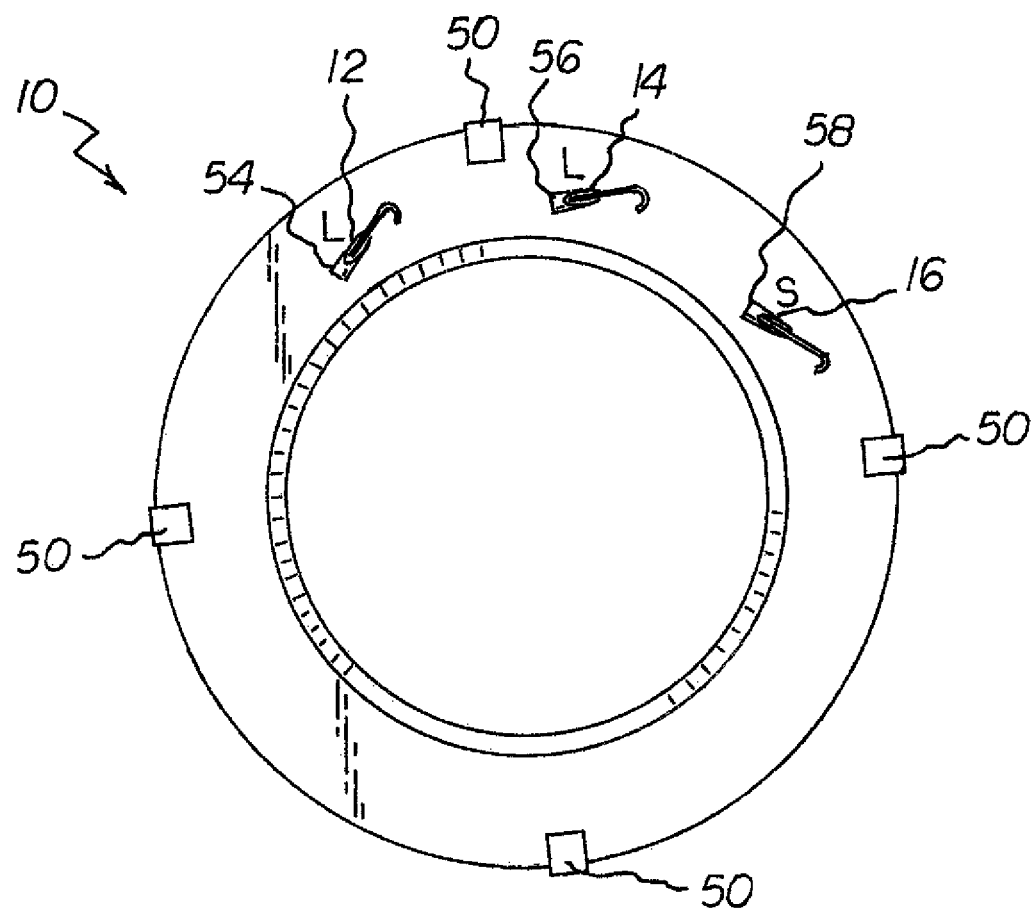
FIG. 2 is a plan view of the system taken along line 2-2 of FIG. 1.
Figure 3:
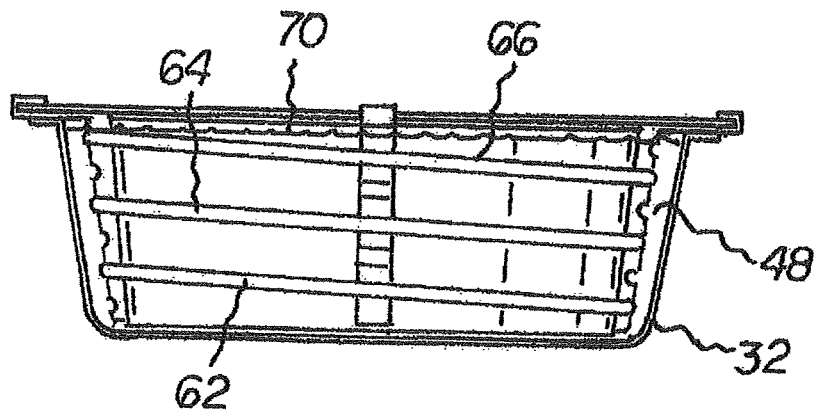
FIG. 3 is a cross sectional view of the system taken along line 3-3 of FIG. 1.
Figure 4:
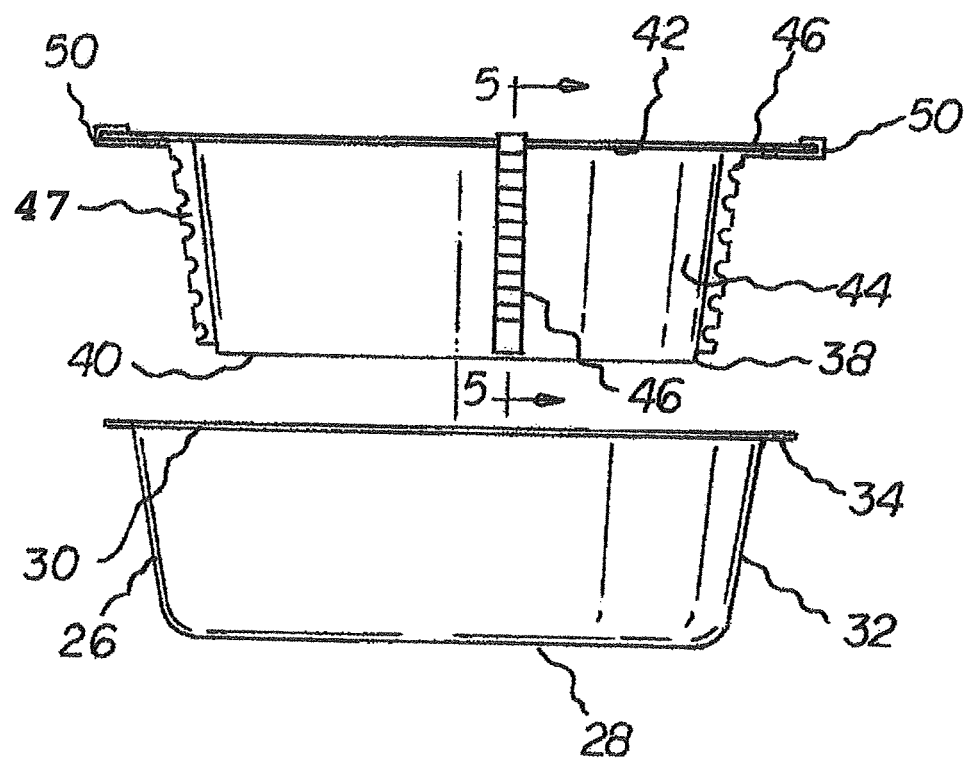
FIG. 4 is an exploded side elevational view of the system shown in FIG. 2.
Figure 5:
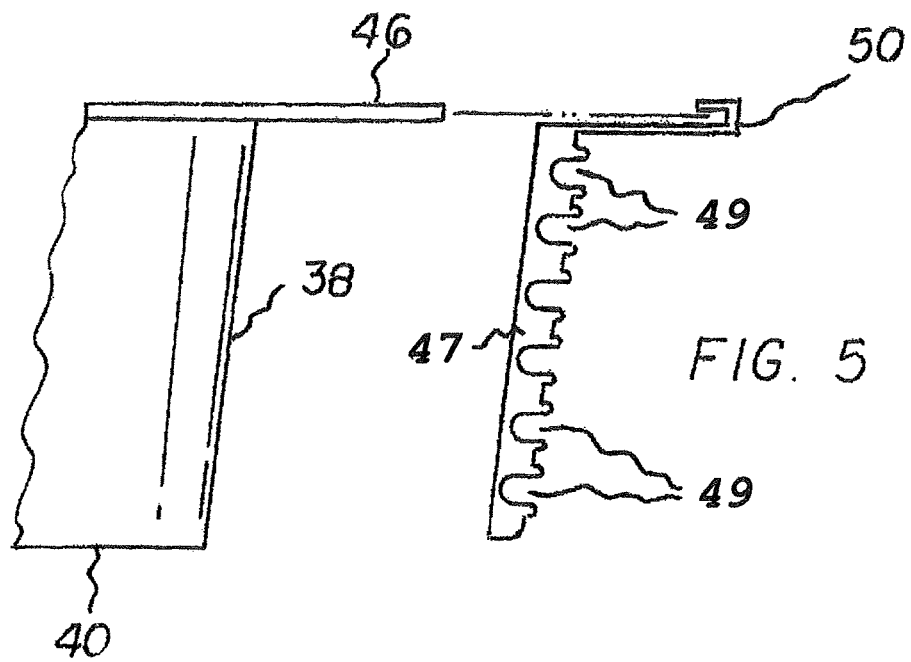
FIG. 5 is an enlarged showing of a support bar and associated components.
Figure 6:
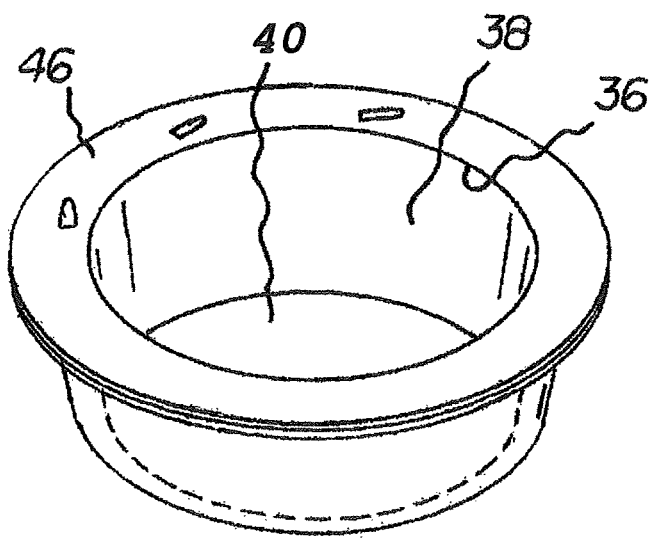
FIG. 6 is a perspective illustration of the Calypso bowl system shown in the prior Figures.

With reference now to the drawings, and in particular to FIG. 1 thereof, the preferred embodiment of the new and improved Calypso Bowl System embodying the principles and concepts of the present invention and generally designated by the reference numeral 10 will be described.

The present invention, the Calypso Bowl System 10 is comprised of a plurality of components. Such components in their broadest context include an exterior bowl, an interior bowl, and tubing. Such components are individually configured and correlated with respect to each other so as to attain the desired objective.

From a specific perspective, present invention is a Calypso Bowl System 10 for supporting a plurality of surgical wires 12, 14, 16 and for dispensing individual surgical wires from the plurality of surgical wires. The supporting and the dispensing is done in a safe, sanitary, convenient, and economical manner.

First provided are the plurality of surgical wires. The plurality of surgical wires include a first surgical wire 12, a second surgical wire 14, and a third surgical wire 16.

First provided is an exterior bowl 26. The exterior bowl has a closed bottom 28, an open top 30, and a side wall 32 there between. An exterior annular flange 34 extends radially outwardly from the open top of the exterior bowl.

Next provided is an interior bowl 38. The interior bowl has an open bottom 40, an open top 42, and a side wall 44 there between. An interior annular flange 46 extends radially outwardly from the open top of the interior bowl. The open bottom of the interior bowl is coupled to the closed bottom of the exterior bowl to create an annular chamber 48 between the side wall of the exterior bowl and the side wall of the interior bowl.

A plurality of support bars 46 are next provided. Each support bar is located within the annular chamber. Each support bar has an inner surface adjacent to the interior bowl. Each support bar has an outer surface formed with recesses 48.

Next, a plurality of clips 50 is provided. Each clip has a lower end attached to an associated one of the support bars. Each clip has an upper end for removably coupling to the interior annular flange.

The interior flange is formed with a plurality of circumferentially spaced apertures 54, 56, 58. The plurality of apertures includes a first aperture 54, a second aperture 56, and a third aperture 58.

Tubing is supported by the recesses. The tubing includes a lowermost tube 62 with a top end and a bottom end, a central tube 64 with a top end and a bottom end, and an uppermost tube 66 with a top end and a bottom end. The top end of the lowermost tube is adjacent to the bottom end of the central tube beneath the first circumferentially spaced aperture. The top end of the central tube is adjacent to the bottom of the uppermost tube beneath the second circumferentially spaced aperture. The top end of the uppermost tube is beneath the third circumferentially spaced aperture.

The first surgical wire 12 extends from the lowermost tube 62 through the first aperture 54. The second surgical wire 14 extends from the central tube 64 through the second aperture 56. The third surgical wire 16 extends from the uppermost tube 66 through the third aperture 58.

Indicia is provided on the interior flange wherein L represents LONG indicating the length of an adjacent surgical wire, and wherein indicia S represents SHORT indicating the length of an adjacent surgical wire.

Lastly, a quantity of saline solution 70 is provided in the annular chamber. In this manner, the plurality of surgical wires within the tubes are submerged in the saline solution.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A Calypso Bowl System comprising:
    an exterior bowl having a closed bottom, an open top, and a side wall there between, an exterior annular flange extending radially outwardly from the open top of the exterior bowl;
    an interior bowl having an open bottom, an open top, and a side wall there between, an interior annular flange extending radially outwardly from the open top of the interior bowl, the open bottom of the interior bowl being coupled to the closed bottom of the interior bowl to create an annular chamber between the side wall of the exterior bowl and the side wall of the interior bowl;
    a plurality of surgical wires; and
    tubing within the chamber in a spiral configuration, the tubing adapted to removably receive the plurality of surgical wires, each of the surgical wires having an upper extent extending upwardly through an associated aperture in the annular flange and out of the annular chamber for being grasped and extracted from the tubing.

2. The system as set forth in claim 1 and further including:
a plurality of support bars, each support bar being located within the chamber, each support bar having an inner surface adjacent to the interior bowl, each support bar having an outer surface formed with recesses supporting the tubing.

3. The system as set forth in claim 2 and further including:
a plurality of clips, each clip having a lower end attached to an associated one of the support bars, each clip having an upper end for removably coupling to the interior annular flange.

4. The system as set forth in claim 1 wherein:
the interior annular flange is formed with a plurality of circumferentially spaced apertures, the circumferentially spaced apertures including a first aperture, a second aperture, and a third aperture; and
the tubing includes a lowermost tube with a top end and a bottom end, the tubing including a central tube with a top end and a bottom end, and the tubing including an uppermost tube with a top end and a bottom end, the top end of the lowermost tube being beneath the first aperture, the top end of the central tube being beneath the second aperture, and the top end of the uppermost tube being beneath the third aperture.

5. The system as set forth in claim 4 wherein the surgical wires include a first surgical wire extending through the first aperture, a second surgical wire extending through the second aperture, and a third surgical wire extending through the third aperture.

6. The system as set forth in claim 5 and further including:
the indicia "L" on the interior flange representing long indicating the length of an adjacent one of the surgical wires;
the indicia "S" on the interior flange representing short indicating the length of an adjacent one of the surgical wire.

7. A Calypso Bowl System (10) for supporting a plurality of surgical wires (12)(14)(16) and for dispensing individual surgical wires from the plurality of surgical wires, the system comprising, in combination:
an exterior bowl (26) having a closed bottom (28), an open top (30), and a side wall (32) there between, an exterior annular flange (34) extending radially outwardly from the open top of the exterior bowl;
an interior bowl (38) having an open bottom (40), an open top (42), and a side wall (44) there between, an interior annular flange (46) extending radially outwardly from the open top of the interior bowl, the open bottom of the interior bowl being coupled to the closed bottom of the exterior bowl to create an annular chamber (48) between the side wall of the exterior bowl and the side wall of the interior bowl;
a plurality of support bars (47), each support bar being located within the annular chamber, each support bar having an inner surface adjacent to the interior bowl, each support bar having an outer surface formed with recesses (49);
a plurality of clips (50), each clip having a lower end attached to an associated one of the support bars, each clip having an upper end for removably coupling to the interior annular flange;
the interior annular flange being formed with a plurality of circumferentially spaced apertures, the plurality of circumferentially spaced apertures including a first aperture (54), a second aperture (56), and a third aperture (58);
tubing supported by the recesses, the tubing including a lowermost tube (62) with a top end and a bottom end, and the tubing also including a central tube (64) with a top end and a bottom end, and the tubing also including an uppermost tube (66) with a top end and a bottom end, the top end of the lowermost tube being adjacent to the first aperture, the top end of the central tube being adjacent to the second aperture, the top end of the uppermost tube being beneath the third aperture;
a plurality of surgical wires including a first surgical wire (12) and a second surgical wire (14) and a third surgical wire (16), the first surgical wire (12) extending through the first aperture (54), and the second surgical wire (14) extending through the second aperture (56), and the third surgical wire (16) extending through the third aperture (58);
indicia "L" on the interior flange representing LONG indicating the length of an adjacent one of the surgical wires, indicia "S" on the interior flange representing SHORT indicating the length of an adjacent one of the surgical wires; and
a quantity of saline solution (70) in the annular chamber whereby the plurality of surgical wires within the tubes are submerged in the saline solution.

* * * * *